(12) United States Patent
Sherpa

(10) Patent No.: US 10,568,570 B1
(45) Date of Patent: Feb. 25, 2020

(54) METHODS AND SYSTEMS FOR PROVIDING A PREFERRED FITNESS STATE OF A USER

(71) Applicant: Trungram Gyaltrul Sherpa, Cambridge, MA (US)

(72) Inventor: Trungram Gyaltrul Sherpa, Cambridge, MA (US)

(*) Notice: Subject to any disclaimer, the term of this patent is extended or adjusted under 35 U.S.C. 154(b) by 0 days.

(21) Appl. No.: 16/276,105

(22) Filed: Feb. 14, 2019

(51) Int. Cl.
| | |
|---|---|
| A61B 5/00 | (2006.01) |
| G06N 20/00 | (2019.01) |
| G06N 5/04 | (2006.01) |
| G16H 50/20 | (2018.01) |
| A61B 5/04 | (2006.01) |
| A61B 5/053 | (2006.01) |

(52) U.S. Cl.
CPC ............ *A61B 5/486* (2013.01); *A61B 5/0002* (2013.01); *A61B 5/0077* (2013.01); *A61B 5/04* (2013.01); *A61B 5/0531* (2013.01); *A61B 5/6802* (2013.01); *A61B 5/7267* (2013.01); *A61B 5/7435* (2013.01); *G06N 5/04* (2013.01); *G06N 20/00* (2019.01); *G16H 50/20* (2018.01); *A61B 2562/0204* (2013.01); *A61B 2562/0219* (2013.01); *A61B 2562/0271* (2013.01)

(58) Field of Classification Search
CPC ................................ A61B 5/486; G16H 50/20
USPC .......................................................... 600/301
See application file for complete search history.

(56) References Cited

U.S. PATENT DOCUMENTS

| | | | |
|---|---|---|---|
| 8,140,143 B2 | 3/2012 | Picard et al. | |
| 8,303,500 B2 | 11/2012 | Raheman | |
| 8,951,164 B2 | 2/2015 | Morris et al. | |
| 9,107,586 B2 | 8/2015 | Tran | |
| 9,165,117 B2 | 10/2015 | Teller et al. | |
| 9,168,001 B2 | 10/2015 | Stivoric et al. | |
| 9,283,429 B2 | 3/2016 | Aragones et al. | |
| 9,283,430 B2 | 3/2016 | Woo et al. | |
| 9,457,256 B2 | 10/2016 | Aragones et al. | |
| 9,655,053 B2 | 5/2017 | Park et al. | |
| 9,737,214 B2 | 8/2017 | Proud | |
| 9,949,691 B2 | 4/2018 | Huppert et al. | |
| 10,004,406 B2 | 6/2018 | Yuen et al. | |
| 10,058,285 B2 | 8/2018 | Horseman et al. | |
| 10,143,405 B2 | 12/2018 | Jayalath et al. | |
| 10,182,726 B2 | 1/2019 | Ahmed et al. | |
| 2006/0183980 A1 | 8/2006 | Yang | |

(Continued)

FOREIGN PATENT DOCUMENTS

WO    2017106781    6/2017

OTHER PUBLICATIONS eGym exercise equipment—What you need to know, website Retrieved from: https://egym.com/en/exercise—equipment/.

*Primary Examiner* — Nadia A Mahmood
(74) *Attorney, Agent, or Firm* — Caldwell Intellectual Property Law

(57) ABSTRACT

Systems and methods for providing a preferred fitness state of a use are disclosed. The system includes at least a sensor that detects at least a biological parameter of a user and a fitness state sorting module that generates a current user fitness state using machine-learning and the at least a biological parameter. Methods of providing a preferred fitness state of a user include detecting at least a biological parameter of a user, determining by a fitness state sorting module a current user fitness state and determining a user specific recommendation by the fitness state sorting module.

13 Claims, 4 Drawing Sheets

(56) References Cited

U.S. PATENT DOCUMENTS

| | | |
|---|---|---|
| 2007/0004969 A1 | 1/2007 | Kong et al. |
| 2012/0215076 A1 | 8/2012 | Yang et al. |
| 2014/0249429 A1* | 9/2014 | Tran .................... A61B 5/0022 |
| | | 600/483 |
| 2015/0272482 A1 | 10/2015 | Houmanfar et al. |
| 2015/0374289 A1 | 12/2015 | Teller et al. |
| 2016/0135738 A1 | 5/2016 | Bowers et al. |
| 2017/0202486 A1 | 1/2017 | Martikka et al. |

* cited by examiner

METHODS AND SYSTEMS FOR PROVIDING A PREFERRED FITNESS STATE OF A USER

FIELD OF THE INVENTION

The present invention generally relates to the field of artificial intelligence. In particular, the present invention is directed to methods and systems for providing a preferred fitness state of a user.

BACKGROUND

When an individual is physically fit, the individual can be healthier overall. However, achieving a particular fitness state can be challenging and individuals are frequently inundated with information about the latest fitness craze in television advertisements and online. Knowing what exercise to perform, how much exercise to perform, and how frequently can be a challenging task to decipher. Additionally, knowing how an individual with certain pre-existing medical conditions will respond and tolerate an exercise routine can pose additional challenges. Similarly, for an individual who has never participated in a fitness regimen before, a similar situation arises. What is desired is a system and method to engage an individual to achieve a particular fitness state, which may be endurance, strength, or well-being based on an individual's biological parameters and current fitness state and goals.

SUMMARY OF THE DISCLOSURE

A system for machine-learning data analysis for determining a fitness state of a user includes at least a sensor designed and configured to detect at least a biological parameter of a user and transmit a data signal containing the at least a biological parameter. The system includes a biological parameter processing module operating on a computing device. The biological parameter processing module is configured to receive the data signal containing at least a biological parameter and parse the data signal to extract the at least a biological parameter of the user. The system includes a demographic processing module operating on the computing device. The demographic processing module is configured to receive at least a user input from the user; the at least a user input includes a desired fitness state of the user. The system includes a fitness state sorting module operating on the computing device. The fitness state sorting module includes a fitness state model relating biological parameters to fitness states. The fitness state sorting module includes a user specific recommendation model relating fitness states to user specific recommendations. The fitness state sorting module is configured to generate a current user fitness state using the fitness state model and the at least a biological parameter and generate a user specific recommendation using the user specific recommendation model and the at least a user input. The system includes user interface configured to provide the current user fitness state and the user specific recommendation to the user.

A system for providing a preferred fitness state of a user includes at least a sensor designed and configured to detect at least a biological parameter of a user and transmit a data signal. They system includes a fitness state sorting module operating on a computing device. The fitness state sorting module includes a fitness state model relating biological parameters to fitness states. The fitness state sorting module is configured to generate a current user fitness state using the fitness state model and the at least a biological parameter.

A method of providing a preferred fitness state of a user includes detecting by at least a sensor, at least a first biological parameter of a user. The method includes receiving by a fitness state sorting module operating on a computing device the at least a biological parameter. The method includes determining by the fitness state sorting module a current user fitness state, where determining the current user fitness state further includes generating the current user fitness state using a fitness state model relating biological parameters to fitness states and determining by the fitness state sorting module a user specific recommendation. Determining the current user specific recommendation further includes generating the user specific recommendation using a user specific recommendation model relating user specific recommendations to fitness states and a goal fitness state.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for providing a preferred fitness state of a user. A sensor is used to detect a biological parameter of a user. One or more machine-learning models relating biological parameters to fitness states determine a current user fitness state using associations derived and/or optimized according to machine-learning protocols. At least a biological parameter may include any measurable category of phenomenon, sign, or characteristic such as a user's heart rate, respiratory rate, brainwave, skin temperature and the like, as described in further detail below. Sensors used to detect at least a biological parameter may include electrophysiologic sensors such as electrocardiograms (ECG or EKG) to detect heart rate, or thermal sensors such as thermometers to detect skin temperature. Fitness state sorting module determines a current user fitness state, and may generate a recommendation based on a user's desired fitness state and/or on a desired fitness state derived from the current fitness state or the at least a biological parameter. For example, a biological parameter showing high blood pressure may be correlated to a fitness state that recommends endurance activity such as running, swimming, and hiking. Fitness state sorting module may determine a user specific recommendation using a user specific recommendation model relating user specific recommendations to fitness states and a goal fitness state. A goal fitness state may be generated by user input, or may be generated using a fitness state model and the at least a biological parameter.

Figure 1:
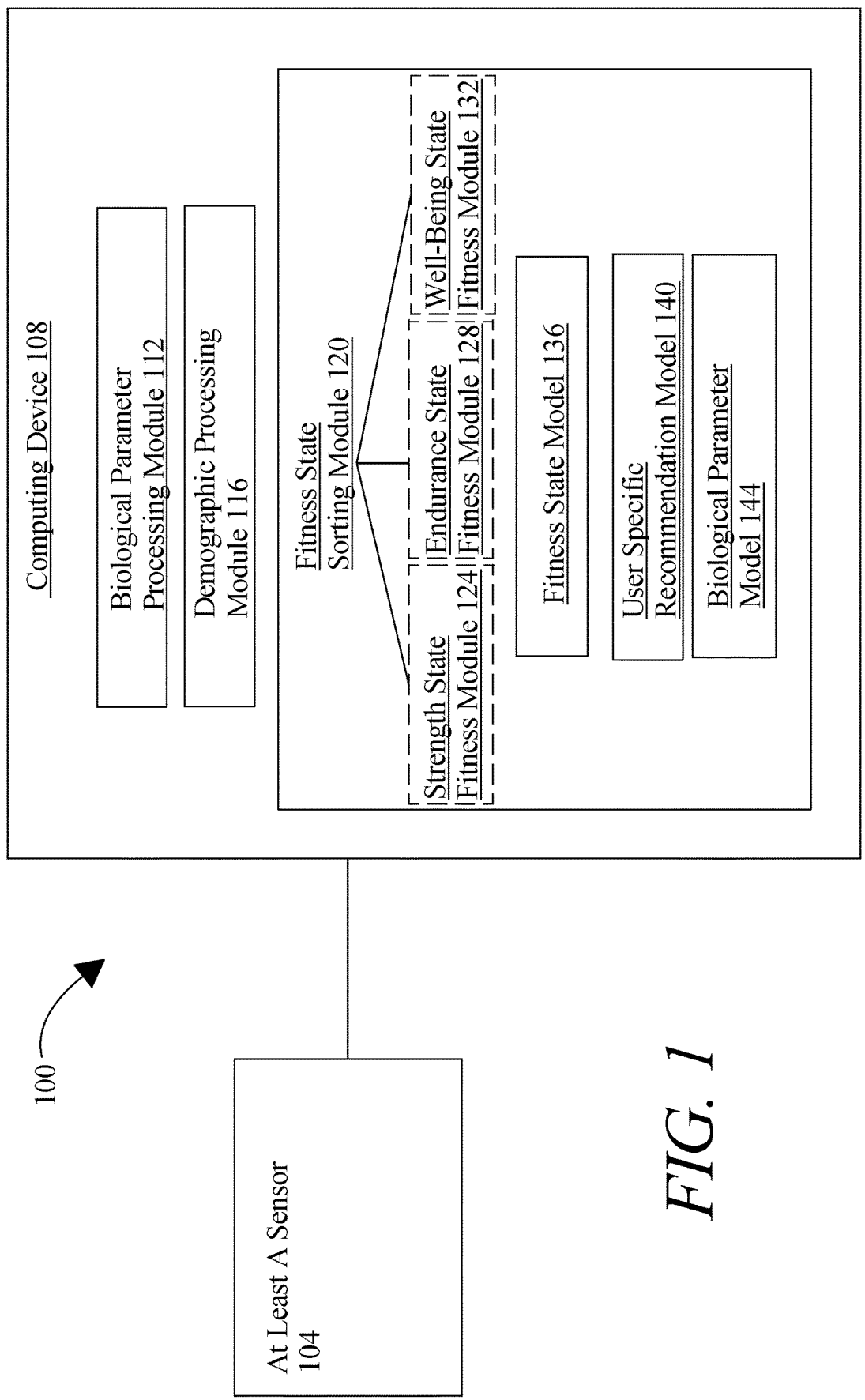
FIG. 1 illustrates a particular embodiment of a system for providing a preferred fitness state of a user.

Referring now to FIG. 1, an exemplary embodiment of a system 100 for providing a preferred fitness state of a user is illustrated. A fitness state as used herein is any state of being of a user as related to physical fitness and wellness. A fitness state may include a user's ability to perform a sport, occupation, daily activities and an exercise. A fitness state may include a user's ability to carry out an activity without undue fatigue. A fitness state may include a user's ability to function efficiently and effectively in work and leisure activities. A fitness state may include a user's ability to perform aerobic and/or anaerobic activities. Aerobic activities may include cardiovascular exercise such as running, swimming cycling and high intensity training. Anaerobic activities may include exercises that build strength, speed and power by building muscle mass and tone. A fitness state of user may be categorized and include one of either a strength state, an endurance state, and a well-being state. Strength state may include a state where a user is physically strong as demonstrated by muscularity, flexibility, and balance. Strength state may include a state that is devoted to muscle building and muscle conditioning, and may include user specific recommendations that highlight anaerobic activities such as weight-bearing exercises, weight-lifting, yoga, squats, lunges, planks, Pilates, push-ups, jumping jacks, rowing, and the like. Endurance state may include a state where a user is able to endure cardiovascular exercise as demonstrated by stamina and resilience. Endurance state may include a state that is devoted to strengthening heart muscle and increasing heart rate through aerobic activities with user specific recommendations that may include running, cycling, elliptical training, high intensity interval training, stair climbing, rope jumping, swimming, circuit training and the like. Well-being state may include a state that is devoted to a mindful state that is devoted to mental clarity and calmness with user specific recommendations that may include activities such as meditation and relaxation, qigong, tai chi, breathing exercises, balancing exercises, martial arts, dance, and the like. A fitness state may include a preferred fitness state, which may include a user's desire to reach a particular state of being as related to physical fitness and wellness. Preferred fitness state may include a user's desire to reach a particular fitness state or fitness level within a fitness state. Preferred fitness state may include a user's goal fitness state. For example, preferred fitness state may include a user's goal to reach a strength state where a user is more flexible and has greater range of movement in certain joints. Preferred fitness state may include a user's desire to reach a specific fitness state such as a strength state or an endurance state, or fitness state may include a user's specific goal directed at a particular fitness state, such as a user's desire to reach an endurance state where a user can run five miles without stopping. A fitness state may include a user's current fitness state, such as what in the present-day user's state of being as related to physical fitness and wellness currently exists.

Still referring to FIG. 1, system 100 includes at least a sensor 104 designed and configured to detect at least a biological parameter of a user and transmit a data signal. As used herein, a sensor is any physical device, module, or system that is designed to detect a condition or state in a user and generates an electrical data signal as a function of the detected condition or state. At least a sensor 104 may detect at least a biological parameter of a user. As used here, at least a biological parameter includes any phenomenon, sign, characteristic, activity, event, or feature that may be sensed from a user's body. This may include any biological process, body condition, physiological state, biochemical response, or any combination thereof. At least a biological process may include for example heart rate or heart beats, heart rate variability (HRV), blood volume pulse (BVP) or blood flow, respiratory rate or breath, brainwave, skin temperature, skin conductivity, eye motion, speech rate, facial expression, and/or body posture. At least a sensor 104 is designed and configured to detect at least a biological parameter of a user and transmit a data signal.

With continued reference to FIG. 1, at least a sensor 104 may include a camera. A camera may be any device that captures pictures, videos or other visual images. Camera may include for example, an electronic device containing a lens that is used to take pictures. Camera may detect body movement of a user, which may be used similarly to body movements detected by at least a motion sensor; camera may, for instance, capture a sequence of images of user's body and compare images of the sequence of images to determine whether user has moved user's body, and if so, how frequently or to what extent. Camera may detect facial expressions of a user, which may determine whether user is over-exerted or unphased by some sort of physical activity for example. Camera may include infrared camera, which may produce thermal images and temperature measurements of a user.

With continued reference to FIG. 1, at least a sensor 104 may include a thermal sensor. Thermal sensor may be any sensor that acquires skin temperature of user's body or a portion thereof. Thermal sensor may include a thermometer. Thermometer may be any device that measures temperature. Thermometer may include for example, a mercury thermometer, an electronic thermometer or an infrared thermometer. Thermal sensor may include, without limitation one or more infrared sensors, which may be composed of thermoelectric/pyroelectric materials or semiconductor devices, such as photodiodes or photoconductors, thermistors, thermocouples, or any other elements or components used in digital and/or electric thermometers or other temperature sensors. Thermal sensor may measure temperature at one or more locations on a user's body. For example, thermal sensor may be placed at or in the mouth, in the ear, in the armpit, and/or in the rectum. Thermal sensor may include non-contact temperature sensors where temperature may be detected or measured remotely, for instance by capturing infrared radiation.

Continuing to refer to FIG. 1, at least a sensor 104 may include an electrophysiological sensor. At least an electrophysiological sensor may be any device or component that measures a physiological parameter of a user and generates an electrical signal as a function of the measurement. At least a physiological parameter may include any information that may be sensed from user's body, including without limitation any electrical, chemical, optical, auditory, olfactory, kinetic, or other information; at least a physiological parameter may include, without limitation, galvanic skin response or skin conductance response, pulse rate, breathing rate, blood flow, heartbeat signatures, electrolyte type and/or concentration, blood metabolite levels or ratios, blood pH level, position and/or balance, body strain, neurological functioning, brain activity, brain waves, blood pressure, cranial pressure, hydration level, auscultatory information, skin and/or core body temperature, facial emotions, eye muscle movement, body movement, blood volume, inhaled and/or exhaled breath volume, exhaled breath physical and/or chemical composition, reflex response sleepiness, response to external stimuli, swallowing volume, swallowing rate, head position or tilt, internal body sounds, functional near-infrared spectroscopy signals, snoring, and/or other physiological information. Electrophysiological sensor may be utilized to detect at least a biological parameter such as heart rate, heart rate variability, blood volume, pulse, respiratory rate or breathing rate, brainwaves, skin temperature, skin conductivity, eye motion, speech rate, facial expression, and/or body posture.

Still referring to FIG. 1, at least an electrophysiological sensor may include, without limitation, a sensor that detects at least an electrical, magnetic, or electromagnetic parameter, state, or reading regarding body of user. At least an electrophysiologic sensor may include an electrodynamic sensor device configured to sense an electrical activity of the heart of a user. For example, the electrodynamic sensor may be configured to sense a heart rate or heart rate variability pattern using electrical activity of the heart, for instance using electrocardiography (ECG or EKG), or conductivity. Electrocardiography may include a process of recording electrical activity of a heart over a period of time using electrodes placed on the skin; electrodes may detect tiny electrical changes on the skin that arise from a heart muscle's electrophysiologic pattern of depolarizing during each heartbeat. An ECG may be used to measure rate and rhythm of heartbeats or other patterns relating to heartbeats, including without limitation heart rate variability patterns. Electrodes may be placed in contact with user's skin using any suitable means, including adhesion or incorporation in a wearable device such as a band of elastic material around user's torso, that places electrodes in contact with user's skin. In some embodiments, direct contact may not be necessary, and electrical functioning may be monitored capacitively, inductively, electromagnetically, or a combination of these approaches. Persons skilled in the art, upon reviewing the entirety of this disclosure, will be aware of various ways in which EKG data may be collected consistently with the instant disclosure.

With continued reference to FIG. 1, at least an electrophysiologic sensor may include a sensor that monitors neurological functioning. As a non-limiting example, electrophysiologic sensor may include one or more sensors that perform an electroencephalogram (EEG); EEG may involve detection of patterns, such as brainwaves, otherwise known as neural oscillations. EEG may be performed by detection of electrical patterns in neural activity using electrodes contacting user's cranium, such as electrodes placed along a forehead of user. Electrodes may be adhered to user or incorporated in a wearable device, such as without limitation an earpiece or item of headgear placing electrodes at cranial locations such as a forehead or temple. In some embodiments, direct contact may not be necessary, and neurological functioning can be monitored capacitively, inductively, electromagnetically, or a combination of these approaches. In some embodiments, brain waves may couple with low frequency acoustical sensors integrated into a head-mounted module, or the like. Persons skilled in the art, upon reviewing the entirety of this disclosure, will be aware of various ways in which EEG data may be collected consistently with the instant disclosure.

Continuing to view FIG. 1, at least an electrophysiologic sensor may include a sensor configured to perform an electrooculogram (EOG); EOG may be defined as an electrophysiologic measurement of eye motion. EOG may be collected using electrodes mounted at or near user's eyes, for instance through use of a mask or other wearable device that contacts the user's eyelids or rests nearby. EOG may be detected through contactless means such as capacitive, inductive, or electromagnetic detection. Alternatively or additionally, at least an electrophysiologic sensor may include electrodes or other sensors for monitoring an electromyogram (EMG) signal measuring electrical activity of muscles or muscular tissue of a user. At least an electrophysiologic sensor may include an electrodermal activity (EDA) sensor, also known as skin conductance, galvanic skin response (GSR) sensor, electrodermal response (EDR) sensor, or the like, which may measure continuous variation in electrical characteristics of skin.

Still viewing FIG. 1, at least an electrophysiological sensor may include one or more sensors configured to detect arterial or vascular data. For instance and without limitation, at least an electrophysiological sensor may include a photoplethysmography (PPG) sensor, which may sense the body's rate of blood flow using a light-based technology whereby a light source is emitted through or at tissue containing blood vessels, and light reflected by or transmitted through the tissue is measured. At least an electrophysiological sensor may include an impedance plethysmograph for measuring changes in volume within an organ or body (usually resulting from fluctuations in the amount of blood or air it contains). For example, an impedance plethysmograph to monitor blood pressure in real-time. At least an electrophysiological sensor may include a sensor to detect pulse oximetry, where pulse oximetry is a standard noninvasive technique of estimating blood gas levels. Pulse oximeters typically employ two or more optical wavelengths to estimate the ratio of oxygenated to deoxygenated blood. Similarly, various types of hemoglobin, such as methemoglobin and carboxyhemoglobin may be differentiated by measuring and comparing the optical absorption at key red and near-infrared wavelengths. Additional wavelengths may be incorporated and/or replace conventional wavelengths. For example, by adding additional visible and infrared wavelengths, myoglobin, methemoglobin, carboxyhemoglobin, bilirubin, $SpCO_2$, and blood urea nitrogen (BUN) may be estimated and/or monitored in real-time in addition to the conventional pulse oximetry.

With continued reference to FIG. 1, at least an electrophysiological sensor may monitor blood pressure, using, as a non-limiting example, a digital blood pressure monitor; digital blood pressure monitor may include actuators and sonic and pressure transducers placed on the skin, and may measure systolic and/or diastolic pressure, for instance by monitoring a pressure at which a "Korotkoff sound" is first heard (systolic), then disappears (diastolic). This technique may also be used to monitor intra-cranial pressure and other internal pressures. Blood pressure may also be measured by comparing the time between pulses at different regions of the body. At least an electrophysiological sensor may alternatively or additionally include pyroelectric sensor for monitoring heart rate, heart rate variability patterns, and the like.

With continued reference to FIG. 1, at least a sensor 104 may include an electrodermal sensor such as a galvanic skin response (GSR), electrodermal response (EDR), psychogalvanic reflex (PGR), skin conductance response (SCR), sympathetic skin response (SSR) and/or skin conductance level (SCL). As used herein, an electrodermal sensor measures continuous variations in electrical characteristics of the skin. This may include but is not limited to measurement of sweating response as controlled by a user's sympathetic nervous system. In an embodiment, changes in sweat response and blood flow response may be measured and recorded as changes in electrical conductance between two points over time. Galvanic skin response (GSR) may include placing two electrodes on a user and applying a weak current, resistance and electrodermal activity may then be recorded. In an embodiment, a painful stimulus may elicit a sympathetic response by sweat glands such as an increase in secretion of sweat containing water and electrolytes. This increase in sweat may then lower electrical resistance of the skin and affect GSR readings. Electrodermal dermal sensor may also detect vasodilation of blood vessels, such as for example during exertion when increase sweating occurs and a user's face may turn red.

Continuing to refer to FIG. 1, at least a sensor 104 may include at least an acoustic sensor, such as a microphone or the like. At least an acoustic sensor may detect and/or monitor breathing characteristics of user, for instance via auscultatory signal extraction. In an embodiment, an acoustic sensor may be used to sense sounds associated with breathing. Signal processing algorithms may then be used to extract breathing sounds from other sounds and noise, for instance using digital signal filtering or noise elimination processes. This information may be used, as a non-limiting example, to measure and/or track intensity, volume, and speed of breathing, which may in turn be used to determine a user's state of exertion, and exercise tolerance. Alternatively or additionally, at least an acoustic sensor may monitor breathing using employ pressure transducers. For instance, and without limitation, changes in pressure inside or near the ear associated with breathing may be measured directly and, through signal processing, translated into a breathing monitor. Similarly, optical reflection sensors may be used to monitor pressure by monitoring physical changes in the skin or tissues in response to breathing. For monitoring the physical changes of the tympanic membrane in response to breathing, and hence ascertaining breathing rate, an optical signal extraction approach may be employed. Microphones can also hear coughing, shortness of breath, troubled breathing during exercise such as wheezing or sputtering and the like.

With continued reference to FIG. 1, at least a sensor 104 may include a motion sensor such as an inertial measurement unit, and/or any component that may be included in an inertial measurement unit. As used herein, an inertial measurement unit measures and reports a body's specific force, angular rate, and magnetic field surroundings the body, An inertial measurement unit may include devices such as a gyroscope and/or an accelerometer. At least a motion sensor may include at least a gyroscope, which may detect orientation changes of the at least a gyroscope; multiple gyroscopes may detect orientation changes with respect to multiple axes, such as three gyroscopes to detect orientation changes with respect to three axes of rotation, or the like. At least a motion sensor may include at least an accelerometer, such as one or more microelectromechanical systems (MEMS) devices. An accelerometer may measure acceleration or position in two or more axes; alternatively or additionally, at least an accelerometer may include a plurality of accelerometers to detect acceleration with respect to a plurality of axes, such as without limitation three accelerometers that detect motion with regard to three dimensional axes. At least a motion sensor may include an inertial measurement unit (IMU), which may include multiple types of motion sensors in a single chip or system. At least a motion sensor may be mounted to one or more parts of user's body to detect motion thereof. Changes in patterns in user motion may indicate a transition by user from one state of wakefulness or sleep to another; for instance, a step towards a deeper sleep state or in a direction transitioning from waking to sleep, as described in further detail below, may be accompanied by a decrease in or cessation of movement by user, and/or by an increased regularity of chest movements indicating regular breathing in a pattern indicative of incipient slumber.

With continued reference to FIG. 1, at least a sensor 104 may include a wearable device. At least a sensor 104 may include any of the sensors as described above. Wearable device may include a sensor worn around a user's neck, waistband, placed in a user's pocket, on a user's wrist and/or on a user's appendage. Wearable device may include at least a sensor 104 that may be incorporated into clothing or worn on the body as an implant or accessory. Wearable device may include but is not limited to glasses containing a pair of lenses set in a frame that may rest on the nose and ears of a user. Wearable device may include a bracelet or wrist watch which may be worn around a user's wrist, and which may be attached by a strap or band. Wearable device may include headphones worn on or around a user's head covering a user's ears. Wearable device may include circumoral headphones, such as those worn around the ear, or supra-aural headphones, such as those worn over the ear. Wearable device may include earbuds which may include individual units that may plug into each of user's ear canals. Wearable device may include shoe insoles inserted into a user's shoes. Wearable device may include a device worn on an appendage, such as a ring worn on a user's finger. Wearable device may include at least a sensor 104 contained in clothing, such as wearable tops, bottoms, and/or accessories worn on a user such as a backpack.

With continued reference to FIG. 1, at least a sensor 104 may transmit a data signal as a function of the at least a biological parameter. Data signal may be transmitted via wired connection to one or more other elements of system 100 as described in more detail below. For example, at least a sensor 104 may include but is not limited to be incorporated in a single electronic device, or mounted on a single chip, microprocessor, microcontroller, and/or digital signal processor (DSP) with one or other additional components of system 100. Alternatively or additionally, data signal may be transmitted to one or more components of system 100 wirelessly. For example, at least a sensor 104 may include one or more wireless transceivers, which may communicate according to protocols such as for example but not limited to BLUETOOTH®, Wi-Fi, Zwave, Li-fi, 6LoWPAN, near-field communication or ZigBee, and may be configured to transmit information wirelessly to one or more other components of system 100. Data signal may be or include a digital signal, such as a packet-based signal. Data signal may include an analog signal, such as an amplitude-modulated or frequency-modulated radio signal. Data signal may be send using any other suitable protocol for electronic transmission of data, including pulse-width modulated signaling or the like. Persons skilled in the art, upon reviewing the entirety of this disclosure, will be aware of various communication protocols that may be used to transmit data signal as consistent with this disclosure.

With continued reference to FIG. 1, system 100 includes a computing device 108 in communication with the at least a sensor 104. Computing device 108 may include any computing device as described below in reference to FIG. 4, including without limitation a microcontroller, microprocessor, digital signal processor (DSP) and/or system on a chip (SoC) as described below in reference to FIG. 4. Computing device 108 may be housed with, may be incorporated in, or may incorporate one or more sensors of at least a sensor. Computing device may include, be included in, and/or communicate with a mobile device such as a mobile telephone or smartphone. Computing device 108 may include a single computing device operating independently, or may include two or more computing device operating in concert, in parallel, sequentially or the like; two or more computing devices may be included together in a single computing device or in two or more computing devices. Computing device 108 may communicate with the at least a sensor 104 through a network interface device. Network interface device may be utilized for connecting a computing device 108 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 108 may include but is not limited to, for example, a computing device 108 or cluster of computing devices in a first location and a second computing device or cluster of computing devices in a second location. Computing device 108 may include one or more computing devices dedicated to data storage, security, distribution of traffic for load balancing, and the like. Computing device 108 may distribute one or more computing tasks as described below across a plurality of computing devices of computing device, which may operate in parallel, in series, redundantly, or in any other manner used for distribution of tasks or memory between computing devices. Computing device 108 may be implemented using a "shared nothing" architecture in which data is cached at the worker, in an embodiment, this may enable scalability of system 100 and/or computing device. Computing device 108 is designed and configured to determine a fitness state of a user as a function of the at least a biological parameter.

With continued reference to FIG. 1, computing device 108 is designed and configured to determine a fitness state of a user a function of the at least a biological parameter. Computing device 108 may include a biological parameter processing module 112 operating on computing device 108. Biological parameter processing module 112 may include any hardware module or logic circuitry. Biological parameter processing module 112 may be instantiated using one or more commands of computer control logic. In an embodiment, biological parameter processing module 112 may be configured to receive a data signal containing at least a biological parameter of a user and parse the data signal to extract the at least a biological parameter of the user. At least a biological parameter of a user of system 100 may be received from the at least a sensor 104. In an embodiment, biological parameter processing module 112 may be in communication with the at least a sensor 104 by a wired or wireless network connection as described below in reference to FIG. 4. Data signal may include the at least a biological parameter of the user. The at least a biological parameter of the user may include any biological parameters as described above in reference to FIG. 1. The at least a biological parameter of the user may be obtained from the user by any of the sensors as described above in reference to FIG. 1. Biological parameter processing module 112 is designed and configured to receive a data signal containing at least a biological parameter of the user and parse the data signal to extract the at least a biological parameter of the user.

With continued reference to FIG. 1, system 100 may include or receive information from one or more additional input elements, such as without limitation wireless communication elements, motion sensors, cameras, antennas and modules for wireless communication including without limitation radio frequency communication, infra-red communication, and/or near-field or radio frequency identification (RFID) communication, or any other sensor elements, input/output elements, or the like that may be incorporated portable computing devices such as smartphones, tablets, or the like.

With continued reference to FIG. 1, system 100 includes a demographic processing module 116 operating on computing device 108. Demographic processing module 116 may include any hardware module or logic circuitry. Demographic processing module 116 may be instantiated using one or more commands of computer control logic. In an embodiment, demographic processing module 116 may be configured to receive a data signal containing at least a user input of the user wherein the at least a user input includes a desired fitness state of the user; desired fitness state may include any fitness state as defined above in reference to FIG. 1. In an embodiment, demographic processing module 116 may parse the data signal to extract the at least a user input of the user. The at least a user input of the user may include any user self-reported information such as age, gender, current fitness state, desired fitness state and the like. User self-reported information may include information including but not limited to user demographics such as age, user health and medical history such as previous diagnosis and chronic illnesses, hospitalizations, medications, surgeries, hospital admissions, and previous fitness regimens and exercise routines. User self-reported information may include user's desired fitness state. For example, user may be new to physical activity and may wish to achieve a well-being state that includes incorporating movement and activity into everyday routines. In yet another non-limiting example, user may be a long-distance runner who is very good at cardiovascular exercises but who has stiff muscles from repeated use and lacks in flexibility. In such an instance, user may be looking to achieve a strength state where user has overall greater flexibility, balance, and physical strength to lift and carry everyday items such as bags of groceries and power tools. User self-reported information may include information user provides as to user's current fitness state and health regimen such as diet, lifestyle, and nutrition habits. User self-reported information may include information from user as to user's response to previous physical activities and exercise routines.

With continued reference to FIG. 1, system 100 includes a fitness state sorting module 120 operating on computing device 108. Fitness state sorting module 120 may include any hardware module or logic circuitry. Fitness state sorting module 120 includes sub-modules consisting of a strength state module 124, an endurance state module 128, and a well-being module 132. Fitness state sorting module 120 includes a machine-learning fitness state model 136 that relates biological parameters to fitness state. Fitness state sorting module 120 includes a machine-learning user specific recommendation model 140 that relates fitness states to user specific recommendations, as described in more detail below. Fitness state sorting module 120 and sub-modules may include any hardware module or logic circuitry. In an embodiment, fitness state sorting module 120 may be designed and configured to generate a current user fitness state using the fitness state model 136 and the at least a biological parameter and generate a user specific recommendation using the user specific recommendation model 140 and the at least a user input. As used herein, fitness-state includes any of the fitness states as used above, and may include one of a strength state fitness module 124, an endurance state fitness module 128, and a well-being state fitness module 132. Strength state fitness module 124 may include any strength state as described above, including without limitation a state where a user is physically strong as demonstrated by muscularity, flexibility, and balance. Strength state fitness module 124 may include a state that is devoted to muscle building and muscle conditioning and may include user specific recommendations that highlight anaerobic activities such as weight-bearing exercises, weight-lifting, yoga, squats, lunges, planks, Pilates, push-ups, jumping jacks, rowing, and the like. Endurance state fitness module 128 may include a state where a user is able to endure cardiovascular exercise as demonstrated by stamina and resilience. Endurance state fitness module 128 may include a state that is devoted to strengthening heart muscle and increasing heart rate through aerobic activities with user specific recommendations that may include running, cycling, elliptical training, high intensity interval training, stair climbing, rope jumping, swimming, circuit training and the like. Well-being state fitness module 132 may include a state that is devoted to a mindful state that is devoted to mental clarity and calmness with user specific recommendations that may include activities such as meditation and relaxation, breathing exercises, qigong, tai chi, martial arts, dance, and the like. Each sub-module fitness state may be broken down into further sub-categories. For example, strength state fitness module 124 may be sub-divided by targeted areas of the body that need to increase in strength, such as muscle groups and may include categories of muscle groups found in similar locations on the body. Such sub-division groups may include a group for the chest shoulders and triceps; a group for the back and biceps; and a group for the hamstrings, calves and glutes. Endurance state fitness module 128 may be sub-divided by recommended exercise activity such as for example but not limited to a group for running, a group for cycling, a group for elliptical training, a group for stair training, a group for high intensity interval training, and the like. Well-being state fitness module 132 may be sub-divided by activity such as for example but not limited to a group for meditation, a group for relaxation, a group for qigong, a group for tai chi, a group for breathing exercises, a group for martial arts, a group for dance, and the like.

With continued reference to FIG. 1, fitness state sorting module 120 may be configured to generate at least an user specific recommendation as a function of a fitness state. As used herein, a user specific recommendation includes any recommended exercise that will aid a user in achieving user's goal fitness state. User specific recommendation may include a sound, voice, visible object, vibration, environmental change, or a combination thereof. In an embodiment a user specific recommendation may include a voice, which may include a teaching, coaching, guidance, instruction, reminder, suggestion, advice, music, or a combination thereof. User specific recommendation may be actionable to a user, such as for example a specific set of exercises such as a stretching sequence or cardiac circuit that is recommended to be performed by a user to reach a preferred fitness state of greater strength or endurance, respectively. User specific recommendation may include guidance such as for example encouragement and support from family and friends. User specific recommendation may aid in preventing a user from harming him or herself, for instance by not encouraging a user to perform an exercise that may be harmful to the user. User specific recommendation may alert a user to a pre-danger or danger zone when a user may need to slow down and/or stop performing exercises and/or other activities according to user specific recommendation. Pre-danger or danger zone may include a state when a user has biological parameters that exceed normal limits, where normal limits may include, without limitation, a number of standard deviations from a mean value for a population of users like user, a number of standard deviations from a mean value for the user, for instance based on statistical processing of data concerning the user, a threshold representing a typical level for a given biological parameter at which risks are elevated for persons generally, persons demographically similar to user, or the like. Data, statistically determined values, and/or thresholds identifying danger or pre-danger zones may be derived using machine learning processes and/or from machine learning models; for instance, and without limitation, user specific recommendation model may provide a user specific recommendation that includes an exercise to be performed and one or more limits within which the exercise should be performed. In an embodiment, user specific recommendation may include a recommendation for a user to slow down when pre-danger and/or danger state is reached. For example, the at least a sensor may detect at least a biological parameter outside of normal limits which may trigger pre-danger or danger zone and user specific recommendation may be for user to slow down exercise. If after a certain amount of time the at least a biological parameter is still outside normal limits local medical personnel such as doctors or emergency room nurses may be alerted and may notify an emergency contact such as a friend or family member. If the at least a biological parameter returns to within normal limits after slowing down, user specific recommendation may then be adjusted so as to avoid a repeat occurrence. In an embodiment medical personnel may be alerted when user exceeds normal limits of biological parameters tailored to user. For example, a user who has heart disease may have a lower pre-danger or danger state for heart rate readings than a healthy user with no history of heart disease. Local authorities such as hospitals or emergency medical personnel may be alerted after a certain period, such as for example when heart rate is elevated for 10 minutes or more. Medical personnel may also be alerted if user is inactive for a certain period, such as if user is laying down on the ground experiencing a heart attack and isn't moving. Medical personnel may be alerted when user exceeds normal limits of biological parameters determined by machine learning and statistical calculations as described immediately above. Computing device 108 may record if user slows down or ignores user specific recommendation and does not slow down. User specific recommendation may include a one-time recommendation or may include a series of repeated suggestions. In an embodiment, an user specific recommendation may be provided to a user in a language selected by a user. For example, a user may select for at last an user specific recommendation to be provided in the Japanese language because user speaks Japanese. In an embodiment, at least an user specific recommendation may be presented as various options, of which a user may select as user's selected user specific recommendation. For example, at least an user specific recommendation may include a list of three different yoga sequences that a user may participate in. User may then select one yoga sequence that user will select as user's user specific recommendation from the three different options. User specific recommendation may include music that may encourage a user to perform user specific recommendation. In an embodiment, music may be provided when user first commences user specific recommendation so as to encourage user to engage in fitness. In yet another non-limiting embodiment, music may be provided as user cools down after performing user specific recommendation. In an embodiment, user may pre-select a user specific recommendation based on various factors such as skill level required to perform at least a user specific recommendation, length of time needed to perform at least a user specific recommendation, equipment necessary to perform at least a user specific recommendation, user's preferred fitness state, and/or user preference for at least a user specific recommendation.

With continued reference to FIG. 1, in an embodiment, at least an user specific recommendation may be adjusted to avoid over-application, under-application, or both. For example, if a user is elderly and/or in poor health, a weaker user specific recommendation may be recommended and may include an instruction spoken slowly. In an embodiment, system 100 may record a history to keep track of how a user responds to the at least an user specific recommendation and may adjust the strength of the at least an user specific recommendation based on a user's history. For example, if a user was irresponsive to the at least a user specific recommendation and continued to stay in a particular fitness state, then system 100 may decide to apply a stronger user specific recommendation potentially with an instruction spoken in a stronger tone. In an embodiment, system 100 may learn from a history of a current session, an accumulated history of prior sessions, or both. In an embodiment, system 100 may present an instruction or teaching in various ways. For example, an instruction or teaching may be presented in different tones, cadence, speed, strength, repetition gap, or a combination thereof.

With continued reference to FIG. 1, fitness state model 136 may utilize a machine learning process to take a training set relating inputs of biological parameters to outputs of fitness states. Machine-learning algorithms may generate correlations, mathematical relationships, and/or other relationships between inputs of biological parameter to outputs of fitness states, may be generated from a training set containing a plurality, which may be thousands or millions, of inputs and related outputs data points; each input may be mapped to a related output in training set. Training set data utilized to generate mathematical algorithms for fitness state model 136 may be obtained from multiple sources such as data obtained from medical journals and medical studies. Sources may include data from fitness tracking equipment that a user may wear. Sources may include statistical data gathered using this system, such as from previous users who have used system 100 to achieve a fitness goal. Sources may include information that is already in the public domain, such as data that is open source and available for the public to use. In an embodiment, system 100 may be updated with data available in real-time from recent publications, journals, and users. In an embodiment, mathematical algorithms and machine learning may be utilized to create relationships and correlations between inputs consisting of biological parameters to outputs consisting of each of strength state fitness module 124, endurance state fitness module 128, and well-being state fitness module 132. Initial training set data obtained for system 100 to generate initial models may be gathered from current medical or scientific journals, data sets already available in the public domain such as open source data, and/or from initial information provided by users. In an embodiment initial training set data may be obtained from one of the previous sources, and/or a combination of any of the previous sources. Fitness state model 136 may be generated by receiving a training set including a plurality of input data containing biological parameters and a plurality of output data containing fitness states associated with the biological parameters of the plurality of input data and generating the fitness state model 136 from the training set using a machine-learning algorithm, as described in further detail below.

Still referring to FIG. 1, fitness state sorting module 120 may include an user specific recommendation model 140. User specific recommendation model 140 may utilize a machine learning process to take a training set relating inputs of fitness states to outputs of user specific recommendations, which also may be generated from thousands or millions of inputs and related output data points. User specific recommendation model 140 may be generated by receiving a training set including a plurality of input data containing fitness states and a plurality of output data containing user specific recommendations associated with the biological parameters of the plurality of input data and generating the user specific recommendation model from the training set using a machine-learning algorithm. In an embodiment, training set data may be utilized to create a machine-learning algorithm relating biological parameters to each fitness state including strength state fitness module 124, endurance state fitness module 128, and well-being state fitness module 132. Training set data utilized to generate mathematical algorithms for fitness state model and/or user specific recommendation model may be obtained from multiple sources such as data obtained from medical journals and medical studies. Sources may include data from fitness tracking equipment that a user may wear. Sources may include statistical data gathered using this system, such as from previous users who have used system 100 to achieve a fitness goal. Sources may include information that is already in the public domain, such as data that is open source and available for the public to use. In an embodiment, system 100 may be updated with data available in real-time from recent publications, journals, and users. In an embodiment, mathematical algorithms and machine learning may be utilized to create relationships and correlations between inputs consisting of biological parameters to outputs consisting of each of strength state fitness module 124, endurance state fitness module 128, and well-being state fitness module 132. Fitness state sorting module 120 may include an user specific recommendation model relating fitness states to user specific recommendations and may be designed and configured to generate a current user fitness state using fitness state model 136 and the at least a biological parameter and generate an user specific recommendation using the user specific recommendation model and a goal fitness level. In an embodiment, fitness state sorting module 120 may be configured to receive a user input including user's goal fitness level. For example, user may provide insight as to what user's fitness goal may be. In an embodiment, fitness state sorting module 120 may be configured to generate goal fitness level using fitness state model 136. For example, fitness state model may relate biological parameters to fitness state and may generate a fitness goal using such data and machine-learning algorithms as described above. For example, a user with a greater than average percent body fat may be related to an endurance fitness state and may receive a fitness goal using data and machine-learning algorithms to suggest a goal such as performing cardiovascular exercise three days each week.

With continued reference to FIG. 1, fitness state sorting module 120 includes biological parameter model 144. Biological parameter model 144 may be generated by receiving a training set including a plurality of input data containing biological parameters and a plurality of output data containing user specific recommendations associated with the plurality of input data and generating the biological parameter model 144 from the training set using a machine-learning algorithm. In an embodiment, training set data may be utilized to create a machine-learning algorithm relating biological parameters to each specific user specific recommendations. Training set data may be obtained from any of the sources as described in more detail above.

With continued reference to FIG. 1, fitness state model 136, user specific recommendation model 140, and/or biological parameter model may be generated by performing a machine-learning process. Machine-learning process may further be performed as a function of context data, circumstances, data, or other information available to system 100 concerning current or past interactions with system 100 and/or third-party processes, platforms, or devices. Machine-learning algorithms as used herein are processes executed by computing devices to improve accuracy and efficiency of other processes performed by the computing devices through statistical or mathematical measures of accuracy and efficiency. Machine learning may function by measuring a difference between predicted answers or outputs and goal answers or outputs representing ideal or "real-world" outcomes the other processes are intended to approximate. Predicted answers or outputs may be produced by an initial or intermediate version of the process to be generated, which process may be modified as a result of the difference between predicted answers or outputs and goal answers or outputs. Initial processes to be improved may be created by a programmer or user or may be generated according to a given machine-learning algorithm using data initially available. Inputs and goal outputs may be provided in two data sets from which the machine learning algorithm may derive the above-described calculations; for instance a first set of inputs and corresponding goal outputs may be provided, and used to create a mathematical relationship between inputs and outputs that forms a basis of an initial or intermediate process, and which may be tested against further provided inputs and goal outputs. Data sets representing inputs and corresponding goal outputs may be continuously updated with additional data; machine-learning process may continue to learn from additional data produced when machine learning process analyzes outputs of "live" processes produced by machine-learning processes. Fitness state sub-module may utilize mathematical relationships between inputs and outputs of system 100 to detect fitness state and generate user specific recommendations. Mathematical relationships between biological parameters and fitness states may modify or optimize that relationship according to a set of biological parameters and a particular fitness state of a user. For example, a biological parameter such as an elevated blood pressure may indicate a fitness state of well-being because of the correlated benefits between a calm mind achieved through exercises such as meditation and qigong and reduced blood pressure. Mathematical relationships between user specific recommendations and fitness states may be utilized to generate user specific recommendations based on a user's determined fitness state. For example, a fitness state such as well-being may be correlated mathematically to user specific recommendations that allow a user to practice exercise that calm the mind and renew the mind-body connection such as meditation and tai-chi. Mathematical relationships between user input and fitness states may be utilized to generate user specific recommendations based on a user's preference for certain activities or dislike for others. User input may also be utilized to select user specific recommendations that may take into account a user's past medical history. For example, a user with a past history of a torn anterior cruciate ligament (ACL) may not be recommend user specific recommendations that are particularly difficult on the knee joint such as basketball, tennis, and running. Other user specific recommendations such as yoga and brisk walking may be selected instead. Mathematical relationships between biological parameters and user specific recommendations may be utilized to select an user specific recommendation based on correlations to biological parameters. For example, a user with a hyper-sweat response may be recommended to user specific recommendations that promote calmness and reduce anxiety such as yoga, and tai-chi. Data utilized to generate mathematical algorithms may be obtained from multiple sources such as data obtained from medical journals and medical studies. Sources may include data from fitness tracking equipment that a user may wear. Sources may include statistical data gathered using this system, such as from previous users who have used system 100 to achieve a goal. Sources may include information that is already in the public domain, such as data that is open source and available for the public to use. In an embodiment, system 100 may be updated with data available in real-time from recent publications, journals, and users.

With continued reference to FIG. 1, machine-learning algorithms used to produce fitness state sorting module 120, fitness state model 136, and/or user specific recommendation model 140 may include linear regression models, which attempt to generate a mathematical relationship relating a linear combination of inputs to goal outputs. Such models may include without limitation ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include lasso models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithm may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, a set of potential actions may be provided for machine-learning algorithms; for instance, a user may enter a set of potential actions representing actions that system 100 may perform or direct another platform or system to perform, making the task of machine-learning algorithm one of matching textual inputs to actions and/or performance of actions. Alternatively or additionally, one or more processes may generate potential new actions based on bodies of input and/or output data, for instance by applying novelty detection methods to determine that a given input is an outlier from other inputs; such processes may, as a non-limiting example, generation of flags indicating that a new class of program action may be needed, or that existing methods are not converging on a particular class. Novelty detection may be performed using, as a non-limiting example, support vector machine novelty detection methods.

With continued reference to FIG. 1, fitness state sorting module 120 utilizing machine learning may include a linear discriminant classifier (LDC), k-nearest neighbor (k-NN), Gaussian mixture model (GMM), discriminant function analysis (DFA), linear discriminate analysis (LDA), classification and regression tree (CART), self-organizing map (SOM), Naïve Bayes algorithm, support vector machine (SVM), artificial intelligence (AI), artificial neural network (ANN), convolutional neural network (CNN), hidden Markov model (HMM), decision tree algorithm, database, knowledge base, vector space model, statistical method, optical flow, active appearance model, deep learning algorithm, and machine learning algorithm.

Still viewing FIG. 1, fitness state sorting module 120 may be configured to calculate or generate one or more sub-module fitness states. A sub-module fitness state may include a first sub-module fitness state generated by a first machine-learning process implementing a first machine-learning methodology and a second sub-module fitness state generated by a second machine-learning process implementing a second machine-learning methodology, wherein the first machine-learning methodology is different from the second machine-learning methodology. For instance, and without limitation, a first machine learning methodology, such as a linear regression process may be more effective at creating a fitness state sub-module for performing a first action, while a second machine learning methodology, such as a convolutional neural net process may produce superior results for a second action. Alternatively or additionally, fitness state sub-module may include a first fitness state sub-module generated by a first machine-learning process implementing a first machine-learning methodology a second fitness state sub-module that is not generated by a machine-learning process; the second fitness state sub-module may, for instance, be created using computer programming or circuit design processes. In an embodiment, fitness state sub-module may have some threshold or minimal competence level may be created by programming or other non-machine learning processes, and replaced by machine-learning generated fitness state sub-modules that are preferentially selected for a given biological parameter for example. In an embodiment, a fitness state sorting module 120 may determine a fitness state sub-module for a given biological parameter based on categorization of biological parameter for a given fitness state sub-module; selection of an appropriate fitness state sub-module may be performed using information generated from biological parameter and user feedback.

With continued reference to FIG. 1, at least one user specific recommendation of the at least a user specific recommendation may be filtered or refined according to one or more additional data concerning user, including without limitation data entered by user. For example, fitness state sorting module 120 and/or user specific recommendation model 140 may utilize user input such as user's hatred for cross country running to ensure that endurance state fitness module 128 sub-module does not recommend cross country running as a possible user specific recommendation. In yet another non-limiting example, fitness state sorting module 120 and/or user specific recommendation model 140 may utilize user input and/or user data such as user's inability to complete a previous user specific recommendation to possibly recommend the user specific recommendation again if necessary. For example, a user who was recommended a user specific recommendation such as practicing yoga three days per week but was only able to practice twice per week, may be once again recommended to practice three days per week if user seeks to achieve a greater strength state fitness module 124.

With continued reference to FIG. 1, system 100 include a network transmission module (not shown) operating on computing device. Network transmission module may include any network interface device such as a network router, network switch, network bridge, network interface card (e.g., a mobile network interface card, a LAN card), a modem, and/or any machine or device capable of routing an electrical signal such as a data signal. Network may include for example but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. Network transmission module may be designed and configured to route at least a data signal to network destinations.

With continued reference to FIG. 1, system 100 may include a memory (not shown). Memory may operate on first server or on another device connected to first server. Memory may include any suitable data structure or databases for storing at least a message, at least a word, and/or circumstance data. Memory may be used for storage and retrieval of context data. As used herein, context data includes any data or information that is time invariant and/or was established in the past. Context data may include, without limitation, user's name, address, fitness history, health history, and/or history of interactions with system 100. History of interactions with system may include past biological parameters detected and tracked by system 100, other characteristics of past interactions such as previously determined fitness state, past user specific recommendations or recommendations generated by system 100 as a function of fitness state, and user response to past fitness state and/or user specific recommendations or recommendations as described in more detail below. Context data may include data associated with user's health history such as for example but not limited to user's history of cardiac disease, respiratory distress, diabetes, and/or other diagnoses or medical events that may affect user's fitness state and/or ability to exercise. Context data may include demographic data. Context data may include past actions taken by user in response to past fitness state and/or previously generated user specific recommendations or recommendations. Context data may include past feedback data provided by user, by other users, or by other parties in communication with system 100, as described in further detail below.

With continued reference to FIG. 1, system 100 includes a user interface. In an embodiment, user interface may be utilized by user to enter user's fitness goals. User interface may be designed and configured to provide the current user fitness state and the user specific recommendation to the user. User interface may be utilized by user to enter user's demographic information, such as that which is received by demographic processing module 116. User interface may, without limitation, include data received, derived, stored, and/or generated by system, including current fitness state, user specific recommendation, goal fitness state, at least a biological parameter to display to user, for instance via a display of a device operated by user. Display may be affected using a web interface, a native application, or any other suitable means or method for display or provision of data to a user as described below in reference to FIG. 4 and/or that may occur to a person skilled in the art upon reviewing the entirety of this disclosure.

Figure 2:
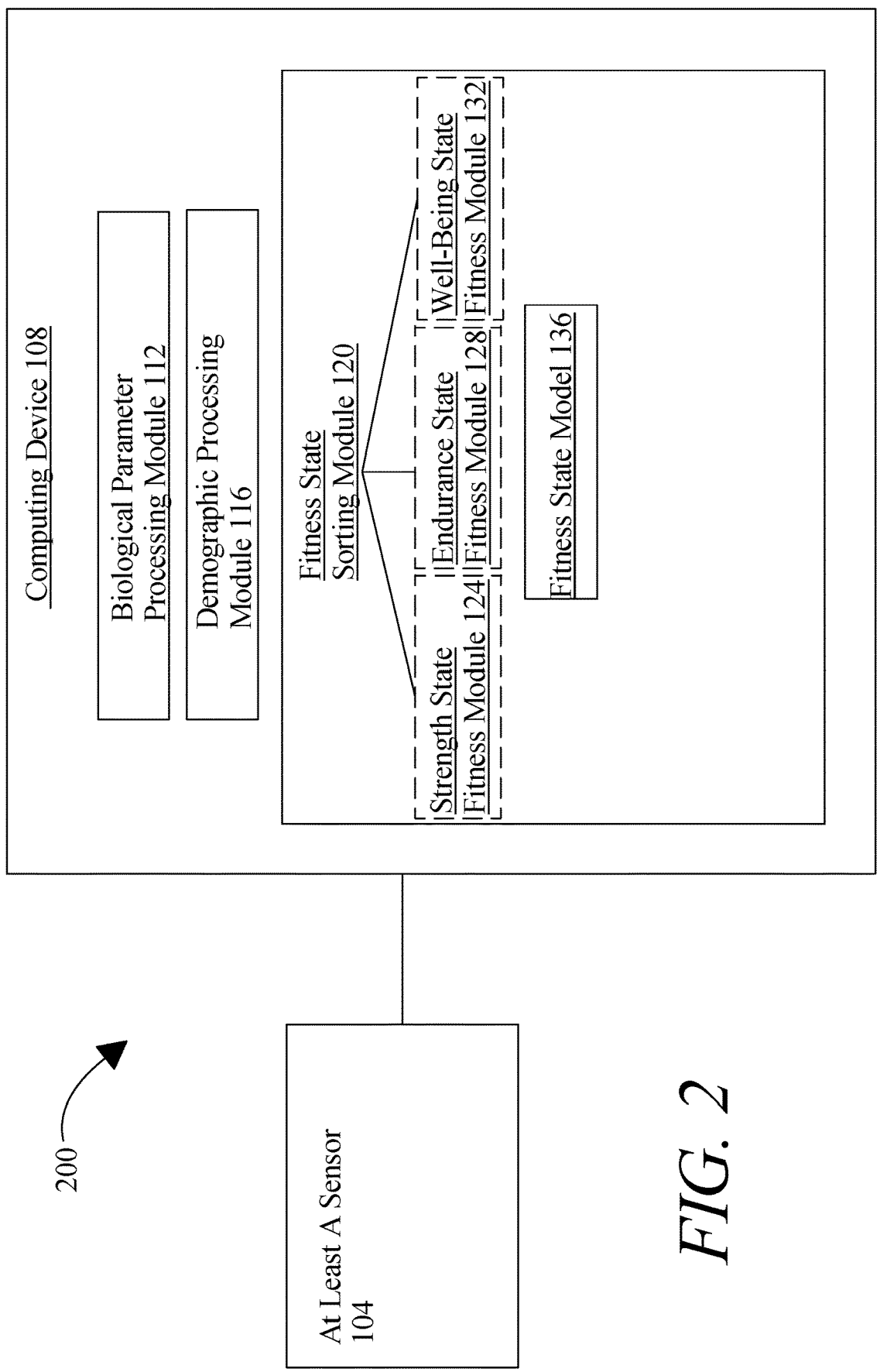
FIG. 2 illustrates a particular embodiment of a system for providing a preferred fitness state of a user.

Referring now to FIG. 2, a system 200 for providing a preferred fitness state of a user is illustrated. System 200 includes at least a sensor 104. The at least a sensor 104 may include any of the sensors 104 as described above in reference to FIG. 1, such as for example but not limited to a camera, a thermal sensor, an electrophysiological sensor, an electrodermal sensor, an acoustic sensor, and/or a motion sensor. In an embodiment, the at least a sensor 104 may be contained within a wearable device. Wearable device may include any of the wearable devices as described above in reference to FIG. 1. In an embodiment, the at least a sensor 104 may be designed and configured to detect at least a biological parameter of a user and transmit a data signal. Data signal may include any of the data signals as described above in reference to FIG. 1.

With continued reference to FIG. 2, system 200 includes a fitness state sorting module 120 operating on a computing device. The fitness state sorting module 120 may include any of the devices or hardware within fitness state sorting module 120 as described above in reference to FIG. 1. Fitness state sorting module 120 includes a fitness state model 136 that uses machine-learning to relate biological parameters to fitness states. Fitness state model 136 may utilize a machine learning as described above using training sets containing one or more data points in FIGS. 1-2. Data points may be obtained from multiple sources such as data obtained from medical journals and medical studies. Sources may include data from system 100. Sources may include data from third-party fitness tracking equipment that a user may wear. Sources may include statistical data gathered using this system, such as from previous users who have used system 100 to achieve a goal. Sources may include information that is already in the public domain, such as data that is open source and available for the public to use. In an embodiment, system 100 may be updated with data available in real-time from recent publications, journals, and users. In an embodiment, mathematical algorithms and machine learning may be utilized to create relationships and correlations between inputs consisting of biological parameters to outputs consisting of each of strength state fitness module 124, endurance state fitness module 128, and well-being state fitness module 132. Fitness state sorting module 120 may be designed and configured to generate a current user fitness state using the fitness state model 136 and the at least a biological parameter. Training set and/or one or more machine-learning models may be updated with entry of further data; for instance, data describing further biological parameter readings, user feedback describing effectiveness or user specific recommendation and/or user data describing fitness state as measured or determined by processes outside of system, such as consultation with doctors and/or personal trainers, may be entered to system 200, and machine-learning processes may iteratively or recursively execute to incorporate new, changed, or corrected data.

Figure 3:
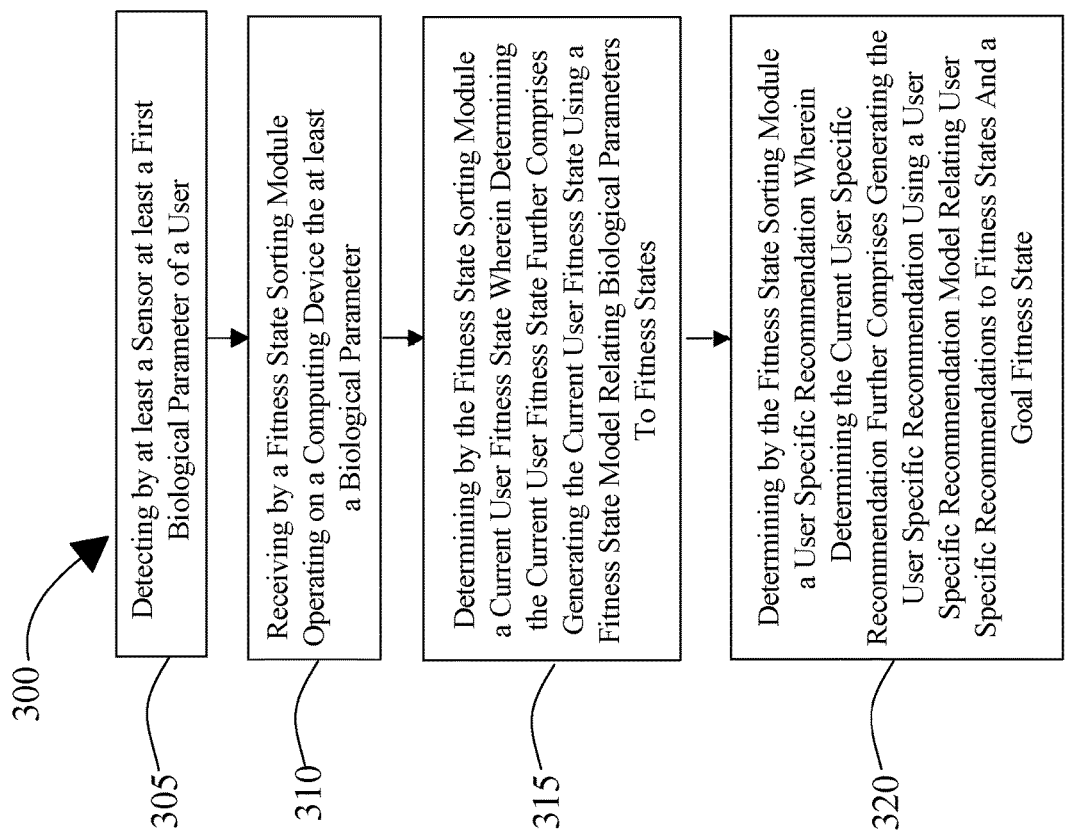
FIG. 3 illustrates a method of providing a preferred fitness state of a user.

Referring now to FIG. 3, a method 300 of providing a preferred fitness state of a user is demonstrated. At step 305 at least a first biological parameter of a user is detected utilizing at least a sensor 104. Biological parameter of a user may include any of the biological parameters as described above in reference to FIGS. 1-2. This may include for example, heart rate, heart rate variability (HRV), blood volume, pulse, respiratory rate or breathing rate, brainwaves, skin temperature, skin conductivity, eye motion, speech rate, facial expression, body posture and the like. At least a biological parameter of a user may be detected utilizing at least a sensor 104. At least a sensor 104 may include any device or component that measures at least a biological parameter of a user and generates an electrical signal as a function of the measurement. At least a sensor 104 may include any of the sensors as described above in reference to FIGS. 1-2 such as a camera, a thermal sensor, an electrophysiological sensor, an electrodermal sensor, an acoustic sensor, a motion sensor and the like. For example, at least an electrophysiological sensor such as an EKG may detect at least a biological parameter of a user such as heart rate and heart rate variability. In an embodiment, EKG may be measured while user is at rest and while user is engaged in exertion such as walking on a treadmill to detect for any abnormalities or differences noted under different conditions. In yet another non-limiting example, at least a sensor 104 may include a thermometer that may detect temperature of user. The at least a sensor 104 may be placed at various locations on user's body. For example, the at least a sensor 104 may be placed on a user's wrist, on a user's neck, and/or on a user's ankle. In an embodiment the at least a sensor 104 may be placed on a limb such as an arm or leg. In yet another non-limiting example, the at least a sensor 104 may be placed at one location on user's body. In yet another example, multiple sensors may be placed at various locations on user's body.

With continued reference to FIG. 3, at step 310 the at least a biological parameter is received by a fitness state sorting module operating on a computing device. Receiving may include receiving a data signal containing the at least a biological parameter of the user. Data signal may include an electrical signal containing the at least a biological parameter of the user. The at least a sensor 104 may transmit data signal via wired or wireless connection to one or more other elements of system 100 such as computing device. For example, the at least a sensor 104 may be but is not limited to be incorporated in a single electronic device, or mounted on a single chip, computing device, microprocessor, microcontroller, and/or digital signal processor (DSP) with one or other additional components of system 100. In an embodiment, the at least a sensor 104 may be contained within computing device 108 whereby the at least a sensor 104 is incorporated into computing device 108. Alternatively or additionally, data signal may be received wirelessly by computing device. For example, at least a sensor 104 may include one or more wireless transceivers, which may communicate according to protocols such as but is not limited to BLUETOOTH®, Wi-Fi, Zwave, Li-fi, 6LoWPAN, near-field communication or ZigBee and may be configured to transmit information wirelessly to one or more other components of system 100 such as computing device, for example. Data signal may be parsed to extract the at least a biological parameter. Processes for parsing may include identification of one or more readings or results; readings or results may be chosen using one or more processes for determining relevance or significance of a particular result, data set, or combinations, which may be weighted by tf-idf or similar measures to assess statistical significance. Significance of certain measurements or results may also be determined by assessment during machine-learning processes of relationships between particular biological parameters and results obtained; that is, where a machine-learning process identifies a relationship between a particular biological parameter and one or more actions to be performed by system 100 for the purposes of accuracy or efficiency, then that particular result may be treated as a significant result and thus extracted as something of significance in its own right. Parsing may further include exclusion of particular results such as biological parameters that do not result in obtaining any results, such as for example a blood pressure reading that is unable to determine a user's blood pressure. Parsing may further include exclusion of particular results that are the same as previously obtained results, or certain results that are outliers as compared to all results obtained. Parsing may also include averaging multiple results, such as for example if three separate blood pressure readings are obtained. In yet another non-limiting example parsing may include exclude certain outliers in a set of data or results, such as for example five blood pressure readings where four of the five are within normal limits, the fifth outlier may be excluded.

With continued reference to FIG. 3, at step 315 fitness state sorting module determines a current user fitness state. Determining the current user fitness state may include generating the current user fitness state using a fitness state model 136 relating biological parameters to fitness states as described above in FIGS. 1-2. Fitness state may include one of a strength state fitness module 124, endurance state fitness module 128, or well-being state as described above in FIGS. 1-2. Computing device utilizes machine learning to determine current user fitness state as described above in FIGS. 1-2. Determining a fitness state by computing device 108 may include a mathematical relationship between at least a biological parameter and fitness state. For example, the at least a biological parameter showing increased heart rate and an excess body fat percentage may correlate to a "cardiac event risk state" where a fitness state such as an endurance state is appropriate because of the emphasis on cardiovascular exercise and reducing a user's body fat percentage through endurance exercise. Mathematical relationships between at least a biological parameter and fitness state may be utilized to determine a current user fitness state, and/or to select one or more target biological parameters that may be utilized to set as a goal to determine how close user may get to achieving preferred fitness state as described above in FIGS. 1-2. Relationships between inputs and outputs as described directly above may include utilizing training data to track relationships from available data in the aggregate as described above in FIGS. 1-2. Data utilized to correlate relationships such as biological parameters and fitness states, user specific recommendations and fitness states, user input and user specific recommendations, and biological parameters and user specific recommendations may be provided from statistical relationships provided from other sources as described above in FIGS. 1-2. For example, journal articles and medical studies showing cardiovascular exercise and reduced blood pressure and percentage body fat may be utilized as sources. Sources may include data obtained from other users, such as data that comes from fitness tracking equipment or the like. Sources may include open source data, such as collected data that is available regarding certain patient populations and is widely available to the public to use. Sources may include data gathered using this system, such as users who have previously used system 100 to achieve goals and preferred fitness states. For example, system may collect previous users' readings and results and update the information within the system. In an embodiment, multiple sources may be utilized to gather data and calculate correlations and determine relationships.

With continued reference to FIG. 3, at step 320 fitness state sorting module determines a user specific recommendation. Determining the user specific recommendation may include generating the user specific recommendation using a user specific recommendation model 140 relating user specific recommendations to fitness states and goal fitness states as described above in FIGS. 1-2. Mathematical relationships between user specific recommendations and fitness states may also be utilized by fitness state sorting module 120 to select at least a user specific recommendation for a user. For example, a user with increased heart rate and high levels of body fat percentage may need a user specific recommendation that recommends cardiovascular exercise based on its correlation to decreased body fat percentage and its correlation surrounding reduced heart rate and reduced blood pressure. In yet another non-limiting example, a user with an endurance fitness state of a given level may be recommended to have user specific recommendations that include cardiovascular activities such as running, brisk walking, cycling, and/or swimming, all of which may target heart rate. A well-being fitness state may be correlated with user specific recommendations that may emphasize the mind-body connection such as yoga, tai-chi, and qigong. Strength fitness state may be correlated with user specific recommendations that emphasize muscle building such as weightlifting, push-ups, and planks. Mathematical relationships between user input and user specific recommendations may be utilized to recommend user specific recommendations based on user input such as user's preference for certain activities and dislike for others as described above in FIGS. 1-2. For example, user's input regarding user's dislike of cycling may be utilized to recommend user specific recommendations such as swimming and/or walking. In yet another example, user's input regarding user's personal health history of multiple knee injuries during exercise may cause user specific recommendations such as tennis and jogging to not be recommended. Rather, user specific recommendations such as swimming may be more appropriate. Mathematical relationships between biological parameters and user specific recommendations may be utilized to recommend user specific recommendations based on current user fitness state and preferred fitness state as described above in FIGS. 1-2. For example, high percentage body fat may be correlated to recommend user specific recommendations such as swimming and walking that will be easier on the joints than a user specific recommendation that recommends running. Once fitness state of user is determined, a user specific recommendation is selected as a function of the user biological parameter and user input. This may be performed, by using the at least a biological parameter and the at least user input to determine user's current fitness state. For example, a biological parameter showing a user has high blood pressure along with a user's input that user performs movements of daily activities, but has no fitness regimen, may cause current fitness state to be chosen as "endurance" but not at a very advanced level. Computing device may then utilize user's current state to predict a likely goal state based on user's input as to short, medium, and/or long-term goals, as well as correlations between biological parameters and current fitness state as well as preferred fitness state as described above in FIGS. 1-2. For example, in an instance where user performs movements of daily activities but has no fitness regimen, computing device may predict a short-term goal such as increasing user activity to a minimum of 20 minutes three days per week. Computing device may predict a longer-term goal such as achieving a more advanced level of endurance fitness state. User specific recommendation may then be selected using user's preferred fitness state by utilizing mathematical algorithms as described above in FIGS. 1-2 to relate preferred fitness state to user specific recommendation. User specific recommendation may also be selected by utilizing mathematical algorithms as described above to relate user input to user specific recommendation, as well as mathematical algorithms to relate biological parameter and preferred fitness state.

With continued reference to FIG. 3, a goal fitness state may be received from a user; for instance, a goal fitness state may include a preferred fitness state. Receiving goal fitness state may occur at user interface, whereby user may enter inputs pertaining to user's goal fitness state. In an embodiment, goal fitness state may include an immediate or short-term goal to be completed in the very near future. In yet another embodiment, goal fitness state may be a medium-term goal, such as for example a goal to be completed over the course of the next few months. In yet another embodiment, goal fitness state may include a long-term goal that user wishes to achieve within one year for example. In yet another embodiment, goal fitness state may be entered by user without any specific time period as to when user may achieve goal fitness state by. Goal fitness state may also be generated using fitness state model 136 and the at least a biological parameter. Mathematical relationships between the at least a biological parameter and current fitness state of a user can be utilized to project "forward" to determine a user's goal fitness state, and/or "backward" to find one or more target biological parameters to set as goals as described above in FIGS. 1-2. For example, mathematical relationships may be utilized to show a correlation between the at least a biological parameter such as percentage body fat and increased risk of cardiac events. In such an instance, increased risk of cardiovascular disease may prompt a user's "forward" goal fitness state to include cardiovascular health improvement through an endurance state including exercises that reduce percentage body fat. Similarly, the at least a biological parameter such as percentage body fat may be utilized "backward" to set as a goal for a user such as to lose 5% body fat within a certain period of time. Over time, user's fitness state may change as affected by user specific recommendations, fitness states, and biological parameters. In an embodiment, receiving the goal fitness state from a user may include receiving by the at least a sensor a second biological parameter of the user and determining by the fitness state sorting module, an updated fitness state, and providing the updated fitness state to the user. For example, user who has demonstrated adherence to at least a user specific recommendation may wish to check user's progress. In such an instance, a second biological parameter of the user may be received, and an updated fitness state may be determined by the fitness state sorting module. This may occur when user is continuously tracked, such as when user may wear and/or utilize the at least a sensor during exertion to see how user responds to the at least a user specific recommendation. In yet anther example, a second biological parameter of the user may be received after a certain period of time, such as for example after a user has practiced a user specific recommendation for a period of two months.

With continued reference to FIG. 3, biological parameter model 144 may be utilized to relate the at least a biological parameter to at least a user specific recommendation as described above in FIGS. 1-2. In an embodiment, biological parameter model 144 may be utilized by correlating a fitness goal with at least a biological parameter and selecting a user specific recommendation as a function of the at least a biological parameter as described above in FIGS. 1-2. In yet another embodiment, biological parameter model 144 may be utilized by taking one more user specific recommendation generated by user specific recommendation model 140 and applying user specific recommendation to biological parameter model 144 to generate refined and/or additional recommendations or eliminate user specific recommendations that may not agree with a user. For example, at least a biological parameter may indicate that a user cannot perform certain exercises that utilize frequent movement of joints because of joint issues, or a user cannot perform certain user specific recommendations such as running because of cardiovascular disease. In such an instance, biological parameter reflecting these problems and/or issues may be correlated to not provide such user specific recommendations for user. In yet another non-limiting example, user who has at least a biological parameter such as elevated blood pressure may be correlated with a fitness goal to reduce stress and anxiety and may be recommended a user specific recommendation such as meditation and breathing exercises.

With continued reference to FIG. 3, computing device 108 may provide the user specific recommendation to user at the user interface. Providing the at least a user specific recommendation to the user may be done but is not limited to being done electronically on computing device for example. In an embodiment, the at least a user specific recommendation may be provided to the user over a network connection. For example, the at least a user specific recommendation may be provided to the user over a wired or wireless network connection to user's device, such as user's smart phone or user's own computing device. In an embodiment, the at least a user specific recommendation may be provided to the user repeatedly on demand when user may activate for the at least a user specific recommendation to be provided to user, such as for example by pushing a button or transmitting a signal. User specific recommendation may be provided as a one-time recommendation to a user or user specific recommendation may be provided repeatedly. In an embodiment, repeatedly provided user specific recommendations may be modified based on factors such as need, user feedback, subsequent readings of the at least a biological parameter, and preferred fitness state of user.

With continued reference to FIG. 3, computing device 108 may provide a second user specific recommendation responsive to the fitness state of the user changing to another state after a first user specific recommendation is provided. For example, computing device 108 may provide user with a first user specific recommendation with certain recommendations to achieve an endurance state fitness module 128. After practicing first user specific recommendation for several weeks, user may measure at least a biological parameter which may indicate that user's health may be optimized by switching to a strength state fitness module 124 as described in more detail above in reference to FIGS. 1-2. Computing device 108 may provide second user specific recommendation for user to achieve strength state fitness module 124 instead of endurance state fitness module 128. In an embodiment, user specific recommendation may be provided and adjusted while user maintains a certain fitness state. For example, user may receive a user specific recommendation or recommendations with different exercises as user progresses throughout a fitness state. For example, when user first enters an endurance state fitness module 128 user specific recommendation may include specific exercises user should perform three times per week with two-pound weights. As user progresses throughout endurance state fitness module 128 and gains muscle, user specific recommendation may be modified, for example by increasing exercise to be performed five times per week and with ten-pound weights. In yet another non-limiting example, user specific recommendation may recommend different exercise recommendations throughout a specific fitness state. For example, a first user specific recommendation in endurance state fitness module 128 may include recommendations for walking outside, whereas later on a second user specific recommendation may be recommended for the same user still in endurance state fitness module 128 for cycling for sixty minutes four times per week. In an embodiment, user specific recommendations may be adjusted and changed based on feedback received while a user performs a user specific recommendation. For example, user may be continuously monitored by the at least a sensor 104 such as an EKG while user performs a specific user specific recommendation, such as running on a treadmill in an endurance state fitness module 128. In such an example, if the at least a sensor 104 such as EKG detects abnormal changes such as a heart attack or arrhythmia that occurs during the practice of the user specific recommendation, user specific recommendation may be stopped temporarily or even stopped completely and danger or pre-danger level may be alerted. In such an instance, the at least a sensor 104 may be tied in to a local 911 system of local authorities and may alert local medical personnel to arrive on scene and provide treatment to user. In such an instance, user specific recommendation may be stopped completely, and a new user specific recommendation may be provided to user after user receives treatment for a detected condition. In yet another non-limiting example, the at least a sensor 104 may be worn during the duration of the user specific recommendation and may provide feedback to user, such as alerting user as to when user's heart rate exceeds normal limits. In such an instance, user specific recommendation may then be adjusted to account for these fluctuations in heart rate that occur during exertion. In an embodiment, the at least a sensor 104 may provide warnings to user such as when a user reaches a pre-danger and/or danger level. For example, user may be alerted and receive a pre-danger alert when user's heart rate begins to exceed normal limits, and user may receive a danger alert when user's heart rate greatly exceeds normal limits. In such an instance, when user receives a danger alert, a user who is engaged in a user specific recommendation may be stopped and local medical authorities and/or emergency workers may be notified. In an embodiment, mathematical relationships and algorithms using machine learning may be utilized to generate alerts when biological parameters exceed normal limits. For example, mathematical relationships and machine learning may create correlations such as when blood pressure exceeds normal limits for a user based on user's age while exercising. Algorithms may be utilized to generate signals when a pre-danger level is reached and when a danger level is reached based on factors that may include but are not limited to user's age, biological parameter, user specific recommendation, user fitness state, and/or user's gender. Machine-learning, mathematical relationships and algorithms may include any of the machine-learning, mathematical relationships, and algorithms as described above in reference to FIGS. 1-2.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 4:
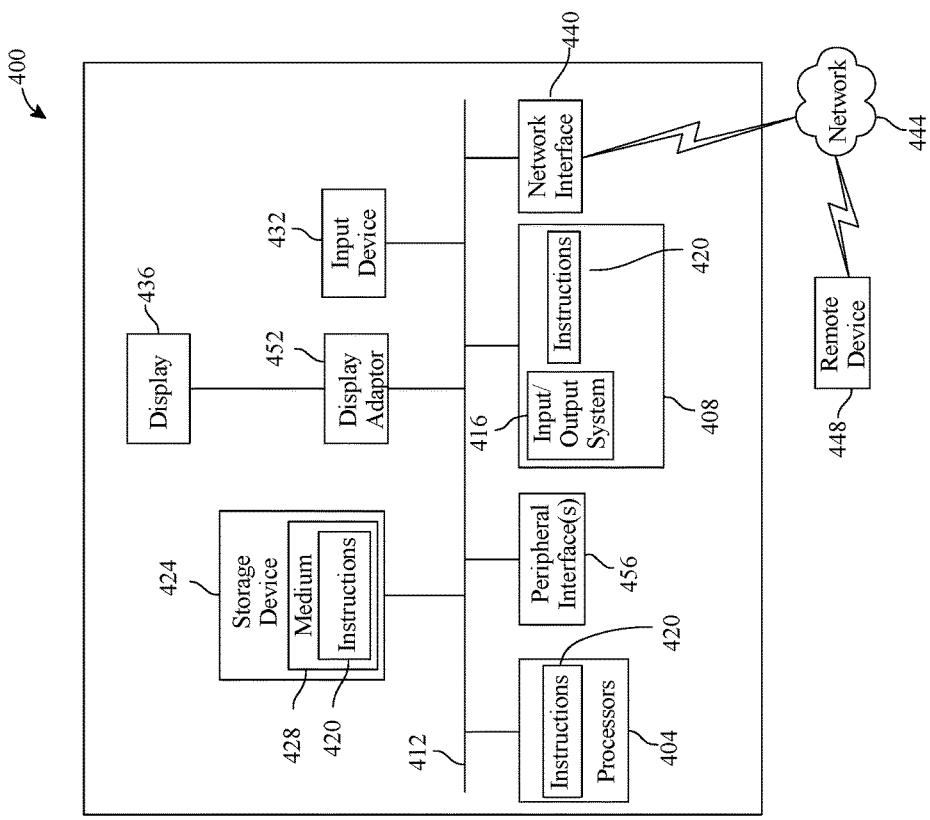
FIG. 4 is a block diagram of a computing system that can be used to implement any one or more of the methodologies disclosed herein and any one or more portions thereof.

FIG. 4 shows a diagrammatic representation of one embodiment of a computing device in the exemplary form of a computer system 400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 400 includes a computing device 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424) include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 628 may provide nonvolatile and/or volatile storage of machine-readable instructions, data structures, program modules, and/or other data for computer system 400. In one example, software 620 may reside, completely or partially, within machine-readable medium 428. In another example, software 420 may reside, completely or partially, within computing device 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIREWIRE interface, a direct interface to bus 412, and any combinations thereof. Input device 432 may include a touch screen interface that may be a part of or separate from display 436, discussed further below.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with computing device 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456.

Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for machine-learning data analysis for determining a fitness state of a user, the system comprising:
   at least a sensor designed and configured to detect at least a biological parameter of a user and transmit a data signal containing the at least a biological parameter;
   a biological parameter processing module operating on a computing device, wherein the biological parameter processing module is configured to:
   receive the data signal containing at least a biological parameter; and
   parse the data signal to extract the at least a biological parameter;
   a demographic processing module operating on the computing device, wherein the demographic processing module is configured to receive at least a user input from the user, wherein the at least a user input includes a desired fitness state of the user;
   a fitness state sorting module operating on the computing device wherein:
   the fitness state sorting module includes a fitness state model relating biological parameters to fitness states;
   the fitness state sorting module includes a user specific recommendation model relating fitness states to user specific recommendations and
   the fitness state sorting module is configured to generate a current user fitness state using the fitness state model and the at least a biological parameter and generate a user specific recommendation using the user specific recommendation model and the at least a user input wherein the at least a user input includes a goal fitness level; and
   a user interface configured to provide the current user fitness state and the user specific recommendation to the user.

2. A system for machine-learning data analysis for determining a fitness state of a user, the system comprising:
   at least a sensor designed and configured to detect at least a biological parameter of a user and transmit a data signal; and
   a fitness state sorting module operating on the computing device wherein:
   the fitness state sorting module includes a fitness state model relating biological parameters to fitness states;
   the fitness state sorting module includes a user specific recommendation model relating fitness states to user specific recommendations;
   the fitness state sorting module is configured to generate a current user fitness state using the fitness state model and the at least a biological parameter and
   the fitness state sorting module is configured to generate a user specific recommendation using the user specific recommendation model and a goal fitness level wherein the fitness state sorting module is configured to generate the goal fitness level using the fitness state model.

3. The system of claim 2, wherein the at least a sensor further comprises a camera.

4. The system of claim 2, wherein the at least a sensor further comprises a thermal sensor.

5. The system of claim 2, wherein the at least a sensor further comprises an electrophysiological sensor.

6. The system of claim 2, wherein the at least a sensor further comprises an electrodermal sensor.

7. The system of claim 2, wherein the at least a sensor further comprises an acoustic sensor.

8. The system of claim 2, wherein the at least a sensor further comprises a motion sensor.

9. The system of claim 2, wherein the at least a sensor further comprises a wearable device.

10. The system of claim 2, wherein the user specific recommendation further comprises a recommended exercise.

11. The system of claim 2, wherein the fitness state sorting module further comprises at least one of a strength state fitness module, an endurance state fitness module, and a well-being fitness state module.

12. The system of claim 1, wherein the fitness state model is generated by:
    receiving a training set including a plurality of input data containing biological parameters and a plurality of output data containing fitness states associated with the biological parameters of the plurality of input data; and
    generating the fitness state model from the training set using a machine-learning algorithm.

13. The system of claim 1, wherein the user specific recommendation model is generated by:
    receiving a training set including a plurality of input data containing fitness states and a plurality of output data containing user specific recommendations associated with the biological parameters of the plurality of input data; and
    generating the user specific recommendation model from the training set using a machine-learning algorithm.

* * * * *